United States Patent [19]
Potter et al.

[11] Patent Number: 5,235,018
[45] Date of Patent: Aug. 10, 1993

[54] POLYISOCYANATES CONTAINING ALLOPHANATE AND ISOCYANURATE GROUPS, A PROCESS FOR THEIR PRODUCTION AND THEIR USE IN TWO-COMPONENT COATING COMPOSITIONS

[75] Inventors: Terry A. Potter, Beaver, Pa.; William E. Slack, Moundsville, W. Va.; Patricia B. Jacobs, Pittsburgh, Pa.

[73] Assignee: Miles Inc., Pittsburgh, Pa.

[21] Appl. No.: 879,659

[22] Filed: May 6, 1992

Related U.S. Application Data

[63] Continuation of Ser. No. 733,566, Jul. 22, 1991, abandoned.

[51] Int. Cl.$^5$ ............................................. C08G 18/08
[52] U.S. Cl. ............................... 528/49; 528/59; 528/67; 528/73; 544/193; 544/196
[58] Field of Search .................. 528/49, 59, 73, 67; 544/193, 196

[56] References Cited

U.S. PATENT DOCUMENTS

| | | | |
|---|---|---|---|
| 3,487,080 | 12/1969 | Matsui et al. | 260/248 |
| 3,996,223 | 12/1976 | Gupta et al. | 260/248 |
| 4,324,879 | 4/1982 | Bock et al. | 528/45 |
| 4,412,073 | 10/1983 | Robin | 544/193 |
| 4,582,888 | 4/1986 | Kase et al. | 528/49 |
| 4,604,418 | 8/1986 | Shindo et al. | 524/296 |
| 4,647,623 | 3/1987 | Kase et al. | 525/123 |
| 4,789,705 | 12/1988 | Kase et al. | 524/590 |
| 5,086,175 | 2/1992 | Minato et al. | 544/221 |

FOREIGN PATENT DOCUMENTS

61-115179 6/1986 Japan.
61-129173 6/1986 Japan.

*Primary Examiner*—Maurice J. Welsh
*Attorney, Agent, or Firm*—Joseph C. Gil; Thomas W. Roy

[57] ABSTRACT

The present invention is directed to a polyisocyanate mixture having an NCO content of 10 to 47% by weight and a viscosity of less than 10,000 mPa.s and containing isocyanurate and allophanate groups in a molar ratio of monoisocyanurates to monoallophanates of 10:1 to 1:5, wherein the allophanate groups are formed from urethane groups which are based on the reaction product of an organic diisocyanate having (cyclo)aliphatic bound isocyanate groups and a monoalcohol containing at least 10 carbon atoms and having a molecular weight of 158 to 2500.

The present invention is also directed to a process for the production of a polyisocyanate mixture having an NCO content of 10 to 47% by weight, having a viscosity of less than 10,000 mPa.s and containing isocyanurate and allophanate groups in a molar ratio of monoisocyanurates to monoallophanates of 10:1 to 1:5 by a) catalytically trimerizing a portion of the isocyanate groups of an organic diisocyanate having (cyclo)aliphatically bound isocyanate groups b) adding 0.001 to 0.5 moles, per mole of organic diisocyanate, of a monoalcohol containing at least 10 carbon atoms and having a molecular weight of 158 to 2500 to the organic diisocyanate prior to or during the trimerization reaction of step a) and c) terminating the trimerization reaction at the desired degree of trimerization by adding a catalyst poison and/or by thermally deactivating the catalyst.

Finally, the present invention is directed to the use of these polyisocyanate mixtures, optionally in blocked form, as an isocyanate components in the two-component coating compositions.

25 Claims, No Drawings

POLYISOCYANATES CONTAINING ALLOPHANATE AND ISOCYANURATE GROUPS, A PROCESS FOR THEIR PRODUCTION AND THEIR USE IN TWO-COMPONENT COATING COMPOSITIONS

This application is a continuation of application Ser. No. 07/733,566, filed Jul. 22, 1991, now abandoned.

BACKGROUND OF THE INVENTION

1. Field of the Invention

The present invention is directed to polyisocyanates which contain allophanate groups and isocyanurate groups and have a low viscosity and improved compatibility with polar and slightly polar solvents and isocyanate-reactive components. The present invention is also directed to a process for the production of these polyisocyanates and their use in two-component coating compositions.

2. Description of the Prior Art

Polyisocyanates containing isocyanurate groups are known and disclosed in U.S. Pat. Nos. 3,487,080, 3,996,223, 4,324,879 and 4,412,073. While these polyisocyanates possess many outstanding properties, they do require improvement in two areas. First, the viscosity of commercially available polyisocyanates containing isocyanurate groups needs to be reduced in order to reduce the amount of solvent which is necessary to obtain a suitable processing viscosity. Presently, there are an increasing number of government regulations which limit the amount of volatile solvents which may be present in coating systems. Therefore, isocyanurate group-containing polyisocyanates may be precluded from certain applications because it is not possible to reduce the viscosity of these polyisocyanates to a suitable processing viscosity without using high amounts of solvent. Second, the isocyanurate group-containing polyisocyanates do not possess sufficient compatibility with highly branched polyester co-reactants as evidenced by the gloss and distinctness of image readings obtained from coatings prepared from these reactants.

It has been proposed in U.S. Pat. No. 4,801,663 to reduce the viscosity of isocyanurate group-containing polyisocyanates prepared from 1,6-hexamethylene diisocyanate (HDI). By terminating the reaction at a very low degree of trimerization higher contents of the monoisocyanurate of HDI are obtained and the quantity of polyisocyanates containing more than one isocyanurate ring is reduced. Because these latter polyisocyanates have a much higher viscosity than the monoisocyanurate, the resulting polyisocyanates have a reduced viscosity. However, a significant disadvantage of this system is that because the reaction is terminated at a very low degree of trimerization, the overall yield is very low and the amount of HDI which must be separated form the product is substantially increased. In other words the small reduction in viscosity is offset by a significant increase in the production cost of the product. Further, the resulting product does not possess optimum compatibility with high branched polyester resins.

Accordingly, it is an object of the present invention to provide polyisocyanates which have a reduced viscosity and improved compatibility with crosslinked polyester co-reactants, while possessing the desirable properties of known polyisocyanates containing isocyanurate groups. It is an additional object of the present invention to provide polyisocyanates which may be produced at reasonable production costs and which are obtained in high yields. Surprisingly, these objectives may be achieved in accordance with the present invention as described hereinafter by the incorporation of specific monoalcohols before or during the trimerization process in order to product a polyisocyanate containing isocyanurate and allophanate groups.

U.S. Pat. No. 4,582,888, 4,604,418, 4,647,623, 4,789,705 are directed the incorporation of various diols in order to improve the compatibility of the resulting polyisocyanates with certain solvents and co-reactants. While the use of diols may improve the compatibility of the polyisocyanates, the diols do not reduce the viscosity of the polyisocyanurates for a given yield.

Many of these references as well as those previously set forth disclose the use of monoalcohols or glycols as co-catalysts for the trimerization reaction. However, none of these references suggest the incorporation of allophanate groups to reduce the viscosity of polyisocyanates containing isocyanurate groups. Further, these references teach that the use of these cocatalysts should be kept to a minimum since the resulting urethane groups reduce the drying time of coatings prepared from the polyisocyanates. In particular, U.S. Pat. No. 4,582,888 cautions against the use of any amount of monoalcohol which is in excess of that needed to dissolve the catalyst.

Japanese Publication 61-151179 discloses the use of monoalcohols containing 6 to 9 carbon atoms as co-catalysts for trimerization catalyst which do not trimerize HDI in the absence of a co-catalyst.

SUMMARY OF THE INVENTION

The present invention is directed to a polyisocyanate mixture having an NCO content of 10 to 47% by weight and a viscosity of less than 10,000 mPa.s and containing isocyanurate and allophanate groups in a molar ratio of monoisocyanurates to monoallophanates of 10:1 to 1:5, wherein the allophanate groups are formed from urethane groups, which are based on the reaction product of an organic diisocyanate having (cyclo)aliphatically bound isocyanate groups and a monoalcohol containing at least 10 carbon atoms and having a molecular weight of 158 to 2500.

The present invention is also directed to a process for the production of a polyisocyanate mixture having an NCO content of 10 to 47% by weight, having a viscosity of less than 10,000 mPa.s and containing isocyanurate and allophanate groups in a molar ratio of monoisocyanurates to monoallophanates of 10:1 to 1:5 by a) catalytically trimerizing a portion of the isocyanate groups of an organic diisocyanate having (cyclo)aliphatically bound isocyanate groups b) adding 0.001 to 0.5 moles, per mole of organic diisocyanate, of a monoalcohol containing at least 10 carbon atoms and having a molecular weight of 158 to 2500 to the organic diisocyanate prior to or during the trimerization reaction of step a) and c) terminating the trimerization reaction at the desired degree of trimerization by adding a catalyst poison and/or by thermally deactivating the catalyst.

Finally, the present invention is directed to the use of these polyisocyanate mixtures, optionally in blocked form, as an isocyanate component in two-component coating compositions.

DETAILED DESCRIPTION OF THE INVENTION

In accordance with the present invention the term "monoisocyanurate" means a polyisocyanate containing one isocyanurate group and formed from three diisocyanate molecules, and the term "polyisocyanurate" means a polyisocyanate containing more than one isocyanurate group. The term "monoallophanate" means a polyisocyanate containing one allophanate group and formed from two diisocyanate molecules and 1 monoalcohol molecule, and the term "polyallophanate" means a polyisocyanate containing more than one allophanate group. The term "(cyclo)aliphatically bound isocyanate groups" means aliphatically and/or cycloaliphatically bound isocyanate groups.

Examples of suitable diisocyanates to be used as starting materials for preparing the polyisocyanates according to the present invention are organic diisocyanates represented by the formula

wherein R represents an organic group obtained by removing the isocyanate groups from an organic diisocyanate having (cyclo)aliphatically bound isocyanate groups and a molecular weight of 112 to 1,000, preferably 140 to 400. Preferred diisocyanates for the process according to the invention are those represented by the above formula wherein R represents a divalent aliphatic hydrocarbon group having from 4 to 18 carbon atoms, a divalent cycloaliphatic hydrocarbon group having from 5 to 15 carbon atoms or a divalent araliphatic hydrocarbon group having from 7 to 15 carbon atoms. Examples of the organic diisocyanates which are particularly suitable for the process include 1,4-tetramethylene diisocyanate, 1,6-hexamethylene, diisocyanate, 2,2,4-trimethyl-1, 6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)methane, α,α,α',α'-tetramethyl,-1,3- and/or -1,4-xylylene diisocyanate, 1-isocyanato-1-methyl-4(3)-isocyanatomethyl cyclohexane, and 2,4- and/or 2,6-hexahydrotoluylene diisocyanate. Mixtures of diisocyanates may also be used. Preferred diisocyanates are 1,6-hexamethylene diisocyanate, isophorone diisocyanate and bis-(4-isocyanatocyclohexyl)methane. 1,6-hexamethylene diisocyanate (HDI) is especially preferred.

It is also possible in accordance with the present invention to use blends of the previously mentioned diisocyanates with monoisocyanates or polyisocyanates having 3 or more isocyanate groups, provided that the isocyanate groups are (cyclo)aliphatically bound.

In accordance with the present invention it is preferred to treat the starting diisocyanates by bubbling an inert gas such as nitrogen through the starting diisocyanate in order to reduce the content of carbon dioxide. This process is discussed in German Offenlegungsschrift 3,806,276 (U.S. application Ser. No. 07/311,920).

Trimerization catalysts which are suitable for the process according to the invention include those previously known such as alkali phenolates of the type described in GB-PS 1,391,066 or GB-PS 1,386,399; aziridine derivatives in combination with tertiary amines of the type described in U.S. Pat. No. 3,919,218; quaternary ammonium carboxylates of the type described in U.S. Pat. Nos. 4,454,317 and 4,801,663; quaternary ammonium phenolates with a zwitterionic structure of the type described in U.S. Pat. No. 4,335,219; ammonium phosphonates and phosphates of the type described in U.S. Pat. No. 4,499,253; alkali carboxylates of the type described in DE-OS 3,219,608; basic alkali metal salts complexed with acrylic organic compounds as described in U.S. Pat. Nos. 4,379,905 such as potassium acetate complexed with a polyethylene glycol which contains an average of 5 to 8 ethylene oxide units; basic alkali metal salts complexed with crown ethers as described in U.S. Pat. No. 4,487,928; aminosilyl group-containing compounds such as aminosilanes, diaminsilanes, silylureas and silazanes as described in U.S. Pat. No. 4,412,073; and mixtures of alkali metal fluorides and quaternary ammonium or phosphonium salts as described in U.S. Ser. No. 07/391,213. Also suitable, though less preferred, are Mannich bases, for example, those based on nonylphenol, formaldehyde and dimethylamine of the type described in U.S. Pat. Nos. 3,996,223 and 4,115,373. The trimerization catalysts should also catalyze the formation of allophanate groups from urethane groups.

Phosphines, such as those described in DE-OS 1,935,763, are not suitable for preparing the products of the present invention. The phosphines, in addition to promoting the trimerization reaction, also promote the dimerization of diisocyanates.

Particularly suitable as catalysts for the process according to the invention are quaternary ammonium hydroxides corresponding to the formula

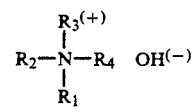

as described in U.S. Pat. No. 4,324,879 and German Offenlegungsschriften 2,806,731 and 2,901,479. Preferred quaternary ammonium hydroxides are those wherein the radicals $R_1$ to $R_4$ represent identical or different alkyl groups having from 1 to 20, preferably from 1 to 4 carbon atoms, which may optionally be substituted by hydroxyl groups. Two of the radicals $R_1$ to $R_4$ may form a heterocyclic ring having from 3 to 5 carbon atoms together with the nitrogen atom and optionally with a further nitrogen or oxygen atom. Also the radicals $R_1$ to $R_3$ in each case may represent ethylene radicals which form a bicyclic triethyelene diamine structure together with the quaternary nitrogen atom and a further tertiary nitrogen atom, provided that the radical $R_4$ then represents a hydroxyalkyl group having from 2 to 4 carbon atoms in which the hydroxyl group is preferably arranged in a 2-position to the quaternary nitrogen atom. The hydroxyl-substituted radical or the hydroxyl-substituted radicals may also contain other substitutents, particularly $C_1$ to $C_4$-alkoxy substituents.

The production of these quaternary ammonium catalysts takes place in known maner by reacting a tertiary amine with an alkylene oxide in an aqueous-alcoholic medium (c.f. U.S. Pat. No. 3,995,997, col. 2, lines 19–44). Examples of suitable tertiary amines include trimethylamine, tributylamine, 2-dimethylaminoethanol, triethanolamine, dodecyldimethylamine, N,N- dimethylcyclohexylamine, N-methylpyrrolidine, N-methylmorpholine and 1,4-diazabicyclo-[2,2,2]-octane. Examples of suitable alkylene oxides include ethylene oxide, propylene oxide, 1,2-butylene oxide, styrene oxide and methoxy, ethoxy or phenoxy propylene oxide. The most preferred catalysts from this group are N,N,N-trimethyl-N-(2-hydroxyethyl)-ammonium hydroxide and N,N,N-trimethyl-N-(2-hydroxypropyl)ammonium hydroxide. Another most preferred catalyst is N,N,N-trimethyl-N-benzyl-ammonium hydroxide.

The trimerization of the starting diisocyanates may be carried out in the absence or in the presence of solvents which are inert to isocyanate groups. Depending on the area of application of the products according to the invention, low to medium-boiling solvents or high-boiling solvents can be used. Suitable solvents include esters such as ethyl acetate or butyl acetate; ketones such as acetone or butanone; aromatic compounds such as toluene or xylene; halogenated hydrocarbons such as methylene chloride and trichloroethylene; ethers such as diisopropylether; and alkanes such as cyclohexane, petroleum ether or ligroin.

The trimerization catalysts are generally used in quantities of about 0.0005 to 5% by weight, preferably about 0.002 to 2% by weight, based on the diisocyanate used. If, for example, a preferred catalyst such as N,N,N-trimethyl-N-(2-hydroxypropyl)-ammonium hydroxide is used, then quantities of about 0.0005 to 1% by weight, preferably about 0.001 to 0.02 by weight, based on starting diisocyanate, are generally sufficient. The catalysts may be used in pure form or in solution. The previously named solvents which are inert to isocyanate groups are suitable as solvents, depending on the type of catalysts. Dimethyl formamide or dimethyl sulphoxide may also be used as solvents for the catalysts.

The simultaneous use of co-catalysts is possible in the process according to the invention, but not necessary. All substances from which a polymerizing effect on isocyanates is known are suitable as co-catalysts such as those described in DE-OS 2,806,731. The co-catalysts are optionally used in a lesser amount on a weight basis in relation to the amount of the trimerization catalyst.

In accordance with the present invention urethane groups and subsequently allophanate groups are incorporated into the polyisocyanates by the use of aliphatic, cycloaliphatic, araliphatic or aromatic monoalcohols. The monoalcohols may be linear, branched or cyclic, contain at least 10 carbon atoms and have a molecular weight of 158 to 2500. The molar ratio of monoalcohol to diisocyanate is about 0.001 to 0.5, preferably about 0.004 to 0.2. Preferred monoalcohols are hydrocarbon monoalcohols and monoalcohols containing ether groups.

The hydrocarbon monoalcohols preferably contain 10 to 36, more preferably 10 to 20 carbon atoms. Examples of suitable monoalcohols include decanol, dodecanol, tetradecanol, hexadecanol, octadecanol, 2,6,8-trimethylnonanol, 2-t-butylcyclohexanol, 4-cyclohexyl-1-butanol, 2,4,6-trimethyl benzyl alcohol, branched chain primary alcohols and mixtures thereof (which are available from Henkel under to Standamul trademark) and mixtures of linear primary alcohols (which are available from Shell under the Neodol trademark).

Suitable ether-containing monoalcohols are those which have a molecular weight of 174 to 2500 and are based on ethylene oxide, propylene oxide and/or butylene oxide.

It is also possible in accordance with the present invention to use mixtures of the previously described monoalcohols with up to 70% by weight, based on the total weight of the alcohol mixture, of monoalcohols containing less than 10 carbon atoms, preferably 1 to 5 carbon atoms, as disclosed in copending application Ser. No. 07/644,174, filed Jan. 22, 1991, now U.S. Pat. No. 5,124,427, 07/895,955, filed Jun. 9, 1992, the disclosures of which are herein incorporated by reference.

When the polyisocyanates containing isocyanurate groups and allophanate groups accordingly to the invention are prepared from monoalcohols containing ethylene oxide units, the polyisocyanates may be dispersed in water as described in copending application, U.S. Pat. No. 5,200,489, the disclosure of which is herein incorporated by reference.

The reaction temperature for isocyanurate and allophanate formation in accordance with the present invention is about 10° to 160° C., preferably about 50° to 150° C. and more preferably about 90° to 120° C.

The process according to the invention may take place either batchwise or continuously, for example, as described below. The starting diisocyanate is introduced with the exclusion moisture and optionally with an inert gas into a suitable stirred vessel or tube and optionally mixed with a solvent which is inert to isocyanate groups such as toluene, butyl acetate, diisopropylether or cyclohexane. The previously described monoalcohol may be introduced into the reaction vessel in accordance with several embodiments. The monoalcohol may be prereacted with the diisocyanate to form urethane groups prior to introducing the diisocyanate into the reaction vessel; the monoalcohol may be mixed with the diisocyanate and introduced into the reaction vessel; the monoalcohol may be separately added to the reaction vessel either before or after, preferably after, the diisocyanate is added; or the catalyst may be dissolved in the monoalcohol prior to introducing the solution into the reaction vessel.

The polyisocyanates according to the invention may also be prepared by blending polyisocyanates containing isocyanurate groups with monoallophonates.

At a temperature of about 60° C. and in the presence of the required catalyst or catalyst solution the trimerization begins and is indicated by an exothermic reaction. As the reaction temperature increases the conversion rate of urethane groups to allophanate groups increases faster than the formation of isocyanurate groups. At temperatures above 85° C. when the desired degree of trimerization is achieved, the urethane groups are generally completely converted to allophanate groups and the product, after removal of unreacted monomer and any solvent present has a low viscosity relative to the yield which is obtained. At temperatures below 85° C. at the same degree of isocyanate group consumption, some urethane groups remain unconverted and the product has a slightly higher, but still low viscosity relative to the yield which is obtained. The progress of the reaction is followed by determining the NCO content by a suitable method such as titration, refractive index or IR analysis. Thus, the reaction may be terminated at the desired degree of trimerization. The termination of the trimerization reaction can take place, for example, at an NCO content of about 15% to 47%, preferably about 20 to 40%.

The termination of the trimerization reaction can take place, for example, by the addition of a catalyst-poison of the type named by way of example in the above-mentioned literature references. For example, when using basic catalysts the reaction is terminated by the addition of a quantity, which is at least equivalent to the catalyst quantity, of an acid chloride such as benzoyl chloride. When using heat-labile catalysts, for example, the previously described quaternary ammonium hydroxides, poisoning of the catalyst by the addition of a catalyst-poison may be dispensed with, since these catalysts decompose in the course of the reaction. When using such catalysts, the catalyst quantity and the reaction temperature are preferably selected such that the catalyst which continuously decomposes is totally decomposed when the desired degree of trimerization is reached. The quantity of catalyst or reaction temperature which is necessary to achieve this decomposition can be determined by a preliminary experiment. It is also possible initially to use a lesser quantity of a heat sensitive catalyst than is necessary to achieve the desired degree of trimerization and to subsequently catalyze the reaction by a further incremental addition of catalyst, whereby the quantity of catalyst added later is calculated such that when the desired degree of trimerization is achieved, the total quantity of catalyst is spent. The use of suspended catalysts is also possible. These catalysts are removed after achieving the desired degree of trimerization by filtering the reaction mixture.

The working-up of the reaction mixture, optionally after previous separation of insoluble catalyst constituents, may take place in various ways depending upon how the reaction was conducted and the area of application for the isocyanates. It is possible to use the polyisocyanates according to the invention which have been produced in solution directly as a lacquer raw material, without a purification stage, if it is not necessary to reduce the free monomer content. Any solvent used during trimerization reaction and any unreacted monomer present in the polyisocyanate product can also be removed by distillation in known manner. The product generally contains a total of less than 2, preferably less than 1% of free (unreacted) monomeric diisocyanates. The products according to the invention have a viscosity of less than 10,000 mPa.s, preferably less than 2000 mPa.s and more preferably less than 1300 mPa.s.

The products according to the present invention are polyisocyanates containing isocyanurate groups and allophanate groups. The products may also contain residual urethane groups which have not been converted to allophanate groups depending upon the temperature maintained during the reaction and the degree of isocyanate group consumption. The ratio of monoisocyanurate groups to monoallophanate groups present in the polyisocyanates according to the invention is about 10:1 to 1:5, preferably about 5:1 to 1:2.

The products according to the invention are valuable starting materials for the production of polyisocyanate polyaddition products by reaction with compounds containing at least two isocyanate reactive groups. Preferred products are most preferably one or two-component polyurethane coatings.

Preferred reaction partners for the products according to the invention, which may optionally be present in blocked form, are the polyhydroxy polyesters, polyhydroxy polyethers, polyhydroxy polyacrylates and optionally low molecular weight, polyhydric alcohols known from polyurethane coatings technology. Polyamines, particularly in blocked form, for example as polyketimines or oxazolidines are also suitable reaction partners for the products according to the invention.

The amounts of the polyisocyanates according to the invention and their reaction partners are selected to provide equivalent ratio of isocyanate groups (whether present in blocked or unblocked form) to isocyanate-reactive groups of about 0.8 to 3, preferably about 0.9 to 1.1.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methylpiperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl caproate, tin(II)-ethyl caproate, dibutyltin(IV)-dilaurate and molybdenum glycolate.

The products according to the invention are also valuable starting materials for two-component polyurethane stoving enamels in which the isocyanate groups are used in a form blocked by known blocking agents. The blocking reaction is carried out in known manner by reacting the isocyanate groups with suitable blocking agents, preferably at an elevated temperature (e.g. about 40° to 160° C.), and optionally in the presence of a suitable catalyst, for example, the previously described tertiary amines or metal salts.

Suitable blocking agents include monophenols such as phenol, the cresols, the trimethylphenols and the tert. butyl phenols; tertiary alcohols such as tert. butanol, tert. amyl alcohol and dimethylphenyl carbinol; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as $\epsilon$-caprolactam and $\delta$-valerolactam; oximes such as butanone oxime and cyclohexanone oxime mercaptans such as methyl mercaptan, ethyl mercaptan, butyl mercaptan, 2-mercaptobenzthiazole, $\alpha$-naphthyl mercaptan and dodecyl mercaptan; and triazoles such as 1H-1,2,4-triazole.

The coating compositions may also contain other additives such as pigments, dyes, fillers, levelling agents and solvents. The coating compositions may be applied to the substrate to be coated in solution or from the melt by conventional methods such as painting, rolling, pouring or spraying.

The coating compositions containing the polyisocyanates according to the invention provide coatings which adhere surprisingly well to a metallic base, and are particularly light-fast, color-stable in the presence of heat and very resistant to abrasion. Furthermore, they are characterized by high hardness, elasticity, very good resistance to chemicals, high gloss, excellent weather resistance and good pigmenting qualities. The polyisocyanates according to the invention also possess good compatibility with high branched polyester resins.

The invention is further illustrated, but is not intended to be limited by the following examples in which all parts and percentages are by weight unless otherwise specified. The use of ppm in the tables refers to the amount of catalyst excluding solvent. The yield was calculated by determining the percentage of free hexamethylene diisocyanate in the product prior to distillation.

EXAMPLES

Example 1

To a 500 ml 3-neck flask equipped with a gas bubbler, mechanical stirrer, thermometer and condenser were added 300 grams of hexamethylene diisocyanate and 43.2 gram of isocetyl alcohol. Dry nitrogen was bubbled through the stirred reaction mixture while it was heated at 60° C. When the urethane reaction was complete (about 1 hour), the temperature was raised to 90° C. To the reaction mixture at 90° C. were added 0.546 grams of a 4.4% solution of trimethylbenzylammonium hydroxide dissolved in 2-butanol. When the reaction mixture reached an NCO content of 33.1%, the reaction was stopped by adding 0.546 grams of di(2-ethylhexyl) phosphate. The excess monomer was removed by thin film evaporation to provide an almost colorless, clear liquid having a viscosity of 700 mPa.s (25° C.), an NCO content of 16.9% and a free monomer (HDI) content of 0.03%. The yield was 54.7%.

Example 2

To a 500 ml 3-neck flask equipped with a gas bubbler, mechanical stirrer, thermometer and condenser were added 300 gram of hexamethylene diisocyanate and 43.2 grams of isocetyl alcohol. Dry nitrogen was bubbled through the stirred reaction mixture while it was heated at 60° C. When the urethane reaction was complete (about 1 hour), the temperature was raised to 90° C. To the reaction mixture at 90° C. were added 0.390 grams of a 4.4% solution of trimethylbenzylammonium hydroxide dissolved in 2-butanol. When the reaction mixture reached an NCO content of 31.3%, the reaction was stopped by adding 0.390 grams of di-(2-ethylhexyl) phosphate. The excess monomer was removed by thin film evaporation to provide an almost colorless, clear liquid having a viscosity of 1490 mPa.s (25° C.), an NCO content of 16.8%, and a free monomer (HDI) content of 0.2%. The yield before distillation, was 68.9%.

Example 3

To a 500 ml 3-neck flask equipped with a gas bubbler, mechanical stirrer, thermometer and condenser were added 300 grams of hexamethylene diisocyanate and 33.3 grams of 1-dodecanol. Dry nitrogen was bubbled through the stirred reaction mixture while it was heated at 60° C. When the urethane reaction was complete (about 1 hour), the temperature was raised to 90° C. To the reaction mixture at 90° C. were added 0.417 grams of a 4.4% solution of trimethylbenzylammonium hydroxide dissolved in 2-butanol. When the reaction mixture reached an NCO content of 33.0%, the reaction was stopped by adding 0.417 grams of di-(2-ethylhexyl) phosphate. The excess monomer was removed by thin film evaporation to provide an almost colorless, clear liquid having a viscosity of 570 mPa.s (25° C., and NCO content of 17.8%, and a free monomer (HDI) content of 0.1%. The yield was 54.8%.

Example 4

To a 2 liter 3-neck flask equipped with a gas bubbler, mechanical stirrer, thermometer and condenser, were added 1000 grams of hexamethylene diisocyanate and 20 grams of a monofunctional poly(ethylene oxide) polyether having an average molecular weight of 464 (started with methanol). Dry nitrogen was bubbled through the stirred reaction mixture for one hour while it was heated to 70° C. At the end of the hour, 6.0 grams of a 4.4% solution of trimethylbenzylammonium hydroxide dissolved in the monofunctional polyether was added to the reaction mixture. An exotherm to 95° C. was observed over 17 minutes and the reaction was cooled to 70° C. over 3 minutes. At that time an NCO content of 40.2% was attained, and the reaction was stopped by addition of 5.1 grams of a 25% solution of di-(2-ethylhexyl)phosphate in hexamethylene diisocyanate. The excess monomer was removed by thin film evaporation to provide an almost colorless, clear liquid having the properties set forth in Table 1.

Example 5

To a 2 liter 3-neck flask equipped with a gas bubbler, mechanical stirrer, thermometer and condenser, were added 1000 grams of hexamethylene diisocyanate and 40 grams of a monofunctional poly(ethylene oxide) polyether having an average molecular weight of 464 (started with methanol). Dry nitrogen was bubbled through the stirred reaction mixture for one hour while it was heated to 70° C. At the end of the hour, 6.0 grams of a 4.4% solution of trimethylbenzylammonium hydroxide dissolved in the monofunctional polyether was added to the reaction mixture. An exotherm to 84° C. was observed over 5 minutes and the reaction was maintained at 82°-84° C. for 20 minutes. At that time an NCO content of 39.0% was attained, and the reaction was stopped by addition of 5.1 grams of a 25% solution of di-(2-ethylhexyl)phosphate in hexamethylene diisocyanate. The excess monomer was removed by thin film evaporation to provide an almost colorless, clear liquid having the properties set forth in Table 1.

EXAMPLE 6

To a 2 liter 3-neck flask equipped with a gas bubbler, mechanical stirrer, thermometer and condenser, were added 1000 grams of hexamethylene diisocyanate and 17.2 grams of 1-butanol. Dry nitrogen was bubbled through the stirred reaction mixture for one and a half hours. Then 23 grams of a monofunctional poly(ethylene oxide) polyether having an average molecular weight of 750 (started with methanol) was added and the reaction was heated to 70° C. To the stirred, heated reaction mixture was added 5.0 grams of 4.4% solution of trimethylbenzylammonium hydroxide dissolved in the 1-butanol. An exotherm to 78° C. was observed over 3 minutes and the reaction was cooled to 75° C. and maintained at 75°-81° C. for 42 minutes. At that time an NCO content of 35.1% was attained, and the reaction was stopped by addition of 4.2 grams of a 25% solution of di-(2-ethylhexyl)phosphate in hexamethylene diisocyanate. The excess monomer was removed by thin film evaporation to provide an almost colorless, clear liquid having the properties set forth in Table 1.

EXAMPLE 7

To a 2 liter 3-neck flask equipped with a gas bubbler, mechanical stirrer, thermometer and condenser, were added 1000 grams of hexamethylene diisocyanate, 17.2 grams of 1-butanol, and 40 grams of a monofunctional poly(ethylene oxide) polyether having an average molecular weight of 750 (started with methanol). Dry nitrogen was bubbled through the stirred reaction mixture for a total of four and a half hours. The reaction was heated to 70° C. To the stirred, heated reaction mixture was added 5.0 grams of 4.4% solution of trimethylbenzylammonium hydroxide dissolved in the 1-butanol. An exotherm to 75° C. was observed over 3 minutes and the reaction was cooled to 66° C. and maintained at 65°-80° C. for two hours and 10 minutes. At that time an NCO content of 33.8% was attained, and the reaction was stopped by addition of 4.2 grams of a 25% solution of di-(2-ethylhexyl)phosphate in hexamethylene diisocyanate. The excess monomer was removed by thin film evaporation to provide an almost colorless, clear liquid having the properties set forth in Table 1.

TABLE 1

| Example No. | p.b.w. polyether/ BuOH per 100 g HDI | Catalyst (ppm) | Crude NCO (%) | Stripped Product | | |
|---|---|---|---|---|---|---|
| | | | | % HDI | Viscosity (mPa · s, 25° C.) | % NCO | Yield (%) |
| 4 | 2.6/0 | 257 | 40.6 | 0.4 | 1280 | 19.9 | 35.5 |
| 5 | 4.6/0 | 252 | 38.6 | 0.3 | 1180 | 19.1 | 41.0 |
| 6 | 2.3/2.2 | 211 | 34.5 | 0.2 | 1820 | 20.0 | 51.0 |
| 7 | 4.0/2.2 | 208 | 33.8 | 0.2 | 1870 | 19.0 | 54.8 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate mixture having an NCO content of 10 to 47% by weight and a viscosity of less than 10,000 mPa.s and containing isocyanurate and allophanate groups in a molar ratio of monoisocyanurates to monoallophanates of 10:1 to 1:5 which comprises
   a) catalytically trimerizing a portion of the isocyanate groups of an organic diisocyanate having (cyclo)aliphatically bound isocyanate groups
   b) adding 0.001 to 0.5 moles, per mole of said organic diisocyanate, of a monoalcohol containing at least 10 carbon atoms and having a molecular weight of 158 to 2500 to said organic diisocyanate prior to or during the trimerization reaction of step a) and
   c) terminating the trimerization reaction at the desired degree of trimerization by adding a catalyst poison and/or by thermally deactivating the catalyst.

2. The process of claim 1 wherein said organic diisocyanate comprises 1,6-hexamethylene diisocyanate.

3. The process of claim 1 wherein said monoalcohol comprises a hydrocarbon monoalcohol containing 10 to 20 carbon atoms.

4. The process of claim 2 wherein said monoalcohol comprises a hydrocarbon monoalcohol containing 10 to 20 carbon atoms.

5. The process of claim 1 wherein said monoalcohol has a molecular weight of 174 to 2500 and contains ether groups.

6. The process of claim 2 wherein said monoalcohol has a molecular weight of 174 to 2500 and contains ether groups.

7. A polyisocyanate mixture having an NCO content of 10 to 47% by weight and a viscosity of less than 10,000 mPa.s and containing isocyanurate and allophanate groups in a molar ratio of monoisocyanurates to monoallophanates of 10:1 to 1:5, wherein said allophanate groups are formed from urethane groups which comprise the reaction product of an organic diisocyanate having (cyclo)aliphatic bound isocyanate groups and a monoalcohol containing at least 10 carbon atoms and having a molecular weight of 158 to 2500.

8. The polyisocyanate mixture of claim 7 wherein said organic diisocyanate comprises 1,6-hexamethylene diisocyanate.

9. The polyisocyanate mixture of claim 7 wherein said monoalcohol comprises a hydrocarbon monoalcohol containing 10 to 20 carbon atoms.

10. The polyisocyanate mixture of claim 8 wherein said monoalcohol comprises a hydrocarbon monoalcohol containing 10 to 20 carbon atoms.

11. The polyisocyanate mixture of claim 7 wherein said monoalcohol has a molecular weight of 174 to 2500 and contains ether groups.

12. The polyisocyanate mixture of claim 8 wherein said monoalcohol has a molecular weight of 174 to 2500 and contains ether groups.

13. A two-component coating composition comprising the polyisocyanate of claim 8 and a compound containing isocyanate-reactive groups.

14. A process for the production of a polyisocyanate mixture having an NCO content of 10 to 47% by weight and a viscosity of less than 10,000 mPa.s and containing isocyanurate and allophanate groups in a molar ratio of monoisocyanurates to monoallophanates of 5:1 to 1:2 which comprises
   a) catalytically trimerizing a portion of the isocyanate groups of an organic diisocyanate having (cyclo)aliphatically bound isocyanate groups
   b) adding 0.001 to 0.5 moles, per mole of said organic diisocyanate, of a monoalcohol containing at least 10 carbon atoms and having a molecular weight of 158 to 2500 to said organic diisocyanate prior to or during the trimerization reaction of step a) and
   c) terminating the trimerization reaction at the desired degree of trimerization by adding a catalyst poison and/or by thermally deactivating the catalyst.

15. The process of claim 14 wherein said organic diisocyanate comprises 1,6-hexamethylene diisocyanate.

16. The process of claim 14 wherein said monoalcohol comprises a hydrocarbon monoalcohol containing 10 to 20 carbon atoms.

17. The process of claim 15 wherein said monoalcohol comprises a hydrocarbon monoalcohol containing 10 to 20 carbon atoms.

18. The process of claim 14 wherein said monoalcohol has a molecular weight of 174 to 2500 and contains ether groups.

19. The process of claim 15 wherein said monoalcohol has a molecular weight of 174 to 2500 and contains ether groups.

20. A polyisocyanate mixture having an NCO content of 10 to 47% by weight and a viscosity of less than 10,000 mPa.s and containing isocyanurate and allophanate groups in a molar ratio of monoisocyanurates to monoallophanates of 5:1 to 1:2, wherein said allophanate groups are formed from urethane groups which comprise the reaction product of an organic diisocyanate having (cyclo)aliphatic bound isocyanate groups and a monoalcohol containing at least 10 carbon atoms and having a molecular weight of 158 to 2500.

21. The polyisocyanate mixture of claim 20 wherein said organic diisocyanate comprises 1,6-hexamethylene diisocyanate.

22. The polyisocyanate mixture of claim 20 wherein said monoalcohol comprises a hydrocarbon monoalcohol containing 10 to 20 carbon atoms.

23. The polyisocyanate mixture of claim 21 wherein said monoalcohol comprises a hydrocarbon monoalcohol containing 10 to 20 carbon atoms.

24. The polyisocyanate mixture of claim 20 wherein said monoalcohol has a molecular weight of 174 to 2500 and contains ether groups.

25. The polyisocyanate mixture of claim 21 wherein said monoalcohol has a molecular weight of 174 to 2500 and contains ether groups.

* * * * *